(12) United States Patent
Lichtner

(10) Patent No.: US 7,905,553 B2
(45) Date of Patent: Mar. 15, 2011

(54) SAFETY GARMENT AND METHOD OF USING THE SAME

(76) Inventor: Elaine Lichtner, Philadelphia, PA (US)

( * ) Notice: Subject to any disclaimer, the term of this patent is extended or adjusted under 35 U.S.C. 154(b) by 362 days.

(21) Appl. No.: 12/061,171

(22) Filed: Apr. 2, 2008

(65) Prior Publication Data
US 2008/0246326 A1    Oct. 9, 2008

Related U.S. Application Data

(60) Provisional application No. 60/921,903, filed on Apr. 5, 2007.

(51) Int. Cl.
*A62B 35/00* (2006.01)
*A47D 15/00* (2006.01)
(52) U.S. Cl. ............ 297/465; 24/298; 24/300; 24/301; 24/302
(58) Field of Classification Search .......... 297/465; 24/298, 300, 301, 302
See application file for complete search history.

(56) References Cited

U.S. PATENT DOCUMENTS

| | | | | |
|---|---|---|---|---|
| 718,948 A | * | 1/1903 | Green | 24/579.11 |
| 2,448,076 A | * | 8/1948 | Bradley | 297/465 X |
| 2,519,687 A | * | 8/1950 | Miller | 24/298 X |
| 2,827,898 A | * | 3/1958 | Thompson | 128/874 |
| 2,868,194 A | | 1/1959 | Lee | |
| 2,908,324 A | * | 10/1959 | Muller et al. | 297/465 |
| 3,085,775 A | * | 4/1963 | Crates et al. | 24/136 R X |
| 3,278,230 A | * | 10/1966 | Boyce et al. | 297/465 |
| 3,380,776 A | * | 4/1968 | Dillender | 297/484 |
| 3,407,807 A | * | 10/1968 | Giberson | 128/874 |
| 3,524,679 A | * | 8/1970 | Lavenne | 297/465 |
| 3,788,309 A | * | 1/1974 | Zeilman | 128/874 |
| 3,827,716 A | | 8/1974 | Vaughn et al. | |
| 3,936,092 A | * | 2/1976 | Dietz | 297/465 |
| 4,143,914 A | * | 3/1979 | Klich | 297/465 |
| 4,324,430 A | | 4/1982 | Dimas, Jr. et al. | |
| 4,550,800 A | | 11/1985 | Dietrich | |
| 4,571,000 A | * | 2/1986 | Holder | 297/465 X |
| D284,326 S | | 6/1986 | Roney et al. | |
| 4,598,945 A | | 7/1986 | Hopkins | |
| 4,655,502 A | | 4/1987 | Houllis | |
| 4,666,207 A | | 5/1987 | Quartano | |
| 4,738,413 A | * | 4/1988 | Spinosa et al. | 297/467 X |
| 4,805,937 A | | 2/1989 | Boucher et al. | |
| D300,474 S | | 3/1989 | Caulder et al. | |
| D300,475 S | | 3/1989 | Caulder et al. | |

(Continued)

FOREIGN PATENT DOCUMENTS
DE    4401702 A1 *  8/1994 .............. 297/465

*Primary Examiner* — Rodney B White
(74) *Attorney, Agent, or Firm* — Duane Morris LLP; Steven E Koffs

(57) ABSTRACT

A safety device includes a garment shaped to be worn on a torso of a user. A flexible strap is attachable to the garment and extends from the garment on first and second sides. The strap has first and second ends. An elongated first fastener component is attached at or near the first end of the strap. An elongated second fastener component is attached at or near the second end of the strap. The first and second fastener components can be rotated to be aligned with, or oblique to, the strap. The first and second fastener components are capable of locking engagement with each other, and are shaped for being used individually as anchors while separated from each other.

26 Claims, 14 Drawing Sheets

U.S. PATENT DOCUMENTS

| | | | |
|---|---|---|---|
| 4,832,053 A * | 5/1989 | McCarthy | 128/869 |
| 4,834,460 A | 5/1989 | Herwig | |
| D302,749 S | 8/1989 | Marquez et al. | |
| 4,854,607 A | 8/1989 | Mandracchia et al. | |
| 4,867,464 A | 9/1989 | Cook | |
| 5,135,075 A | 8/1992 | Aten, Jr. et al. | |
| 5,203,613 A | 4/1993 | Ward | |
| 5,238,293 A | 8/1993 | Gibson | |
| 5,263,726 A | 11/1993 | Wood | |
| 5,272,770 A * | 12/1993 | Allen et al. | 2/421 |
| D343,257 S | 1/1994 | DiFloria et al. | |
| 5,325,818 A | 7/1994 | Leach | |
| 5,378,046 A | 1/1995 | Gordy et al. | |
| 5,379,725 A | 1/1995 | Roberson et al. | |
| 5,421,068 A * | 6/1995 | Menechella | 24/298 |
| 5,547,250 A | 8/1996 | Childers | |
| 5,641,200 A | 6/1997 | Howell | |
| 5,676,426 A | 10/1997 | Herring | |
| 5,678,888 A | 10/1997 | Sowell et al. | |
| 5,829,835 A | 11/1998 | Rogers et al. | |
| 5,890,227 A * | 4/1999 | Brown | 2/102 |
| 5,890,769 A | 4/1999 | Fairbanks | |
| 5,897,165 A | 4/1999 | Kucharczyk et al. | |
| 5,927,235 A | 7/1999 | Olaiz | |
| 5,967,606 A | 10/1999 | Bergh et al. | |
| 6,007,156 A * | 12/1999 | Chang | 297/465 |
| 6,036,264 A | 3/2000 | Lucree | |
| D423,176 S | 4/2000 | Cherry et al. | |
| 6,088,885 A | 7/2000 | Galbreath | |
| 6,186,521 B1 | 2/2001 | Divoky et al. | |
| 6,206,471 B1 | 3/2001 | McGowan | |
| 6,224,152 B1 | 5/2001 | Hughes et al. | |
| 6,237,998 B1 | 5/2001 | Aprile | |
| 6,409,272 B1 | 6/2002 | Martin et al. | |
| 6,499,149 B2 * | 12/2002 | Ashline | 297/465 X |
| 6,513,824 B2 * | 2/2003 | DuBose | 297/465 X |
| 6,902,193 B2 * | 6/2005 | Kim et al. | 297/465 X |
| 7,073,866 B1 | 7/2006 | Berdahl | |
| 7,137,394 B2 | 11/2006 | Graupner et al. | |
| 7,210,707 B2 * | 5/2007 | Schroth | 297/484 X |
| 2001/0048235 A1 | 12/2001 | Hartranft | |
| 2004/0135407 A1 | 7/2004 | Hunter et al. | |
| 2005/0179244 A1 * | 8/2005 | Schroth | 297/465 X |
| 2005/0275261 A1 | 12/2005 | Graupner et al. | |
| 2007/0017001 A1 | 1/2007 | Wagner et al. | |
| 2007/0085408 A1 * | 4/2007 | Kohani | 297/465 |

* cited by examiner

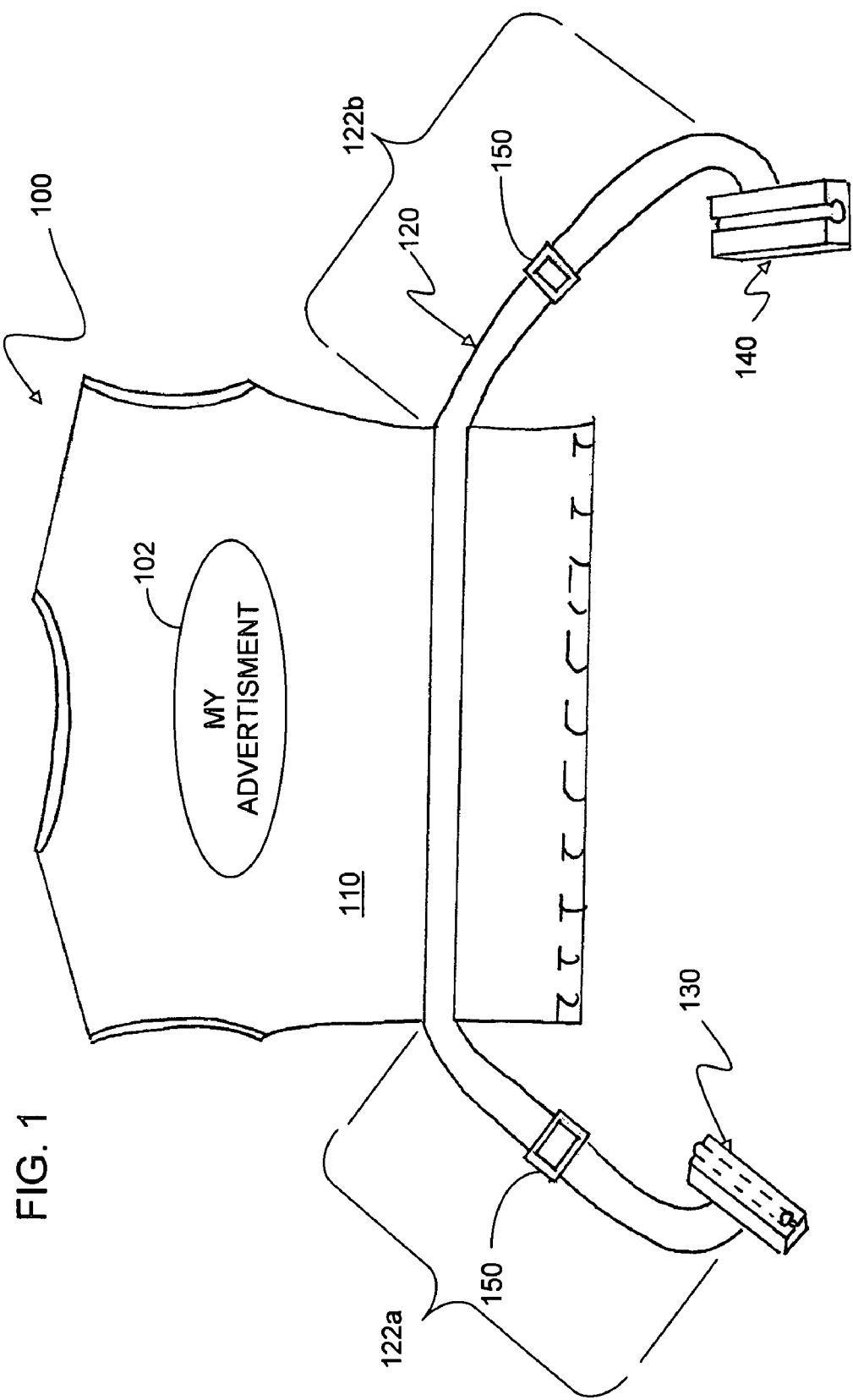

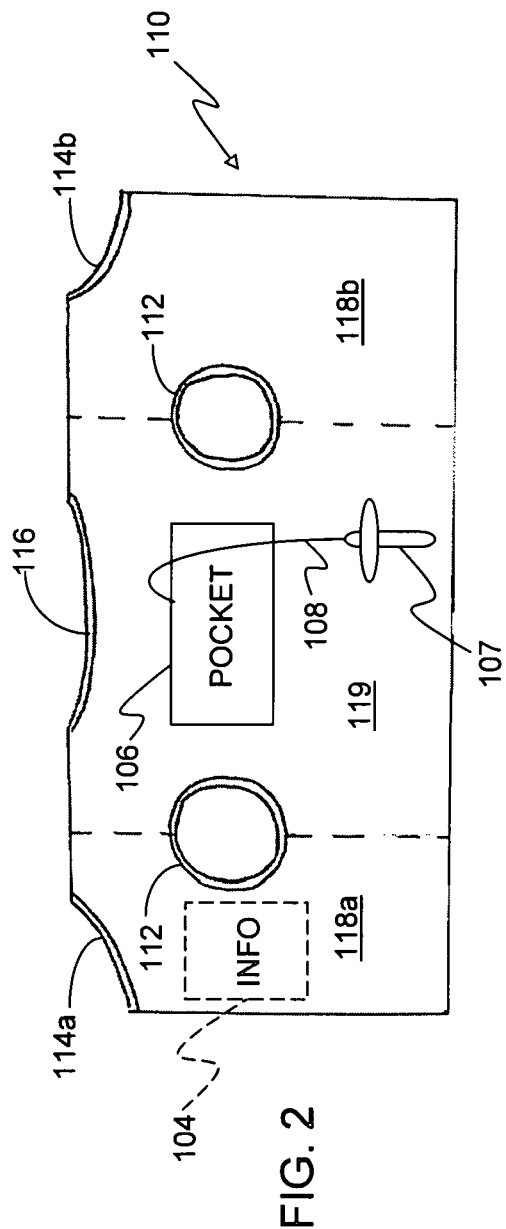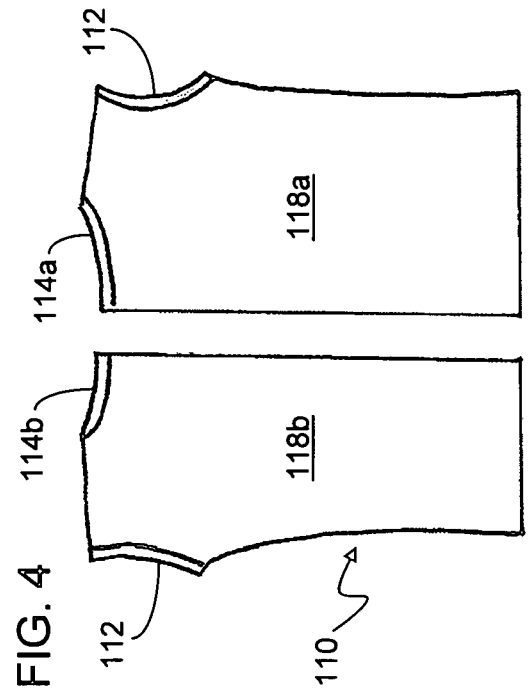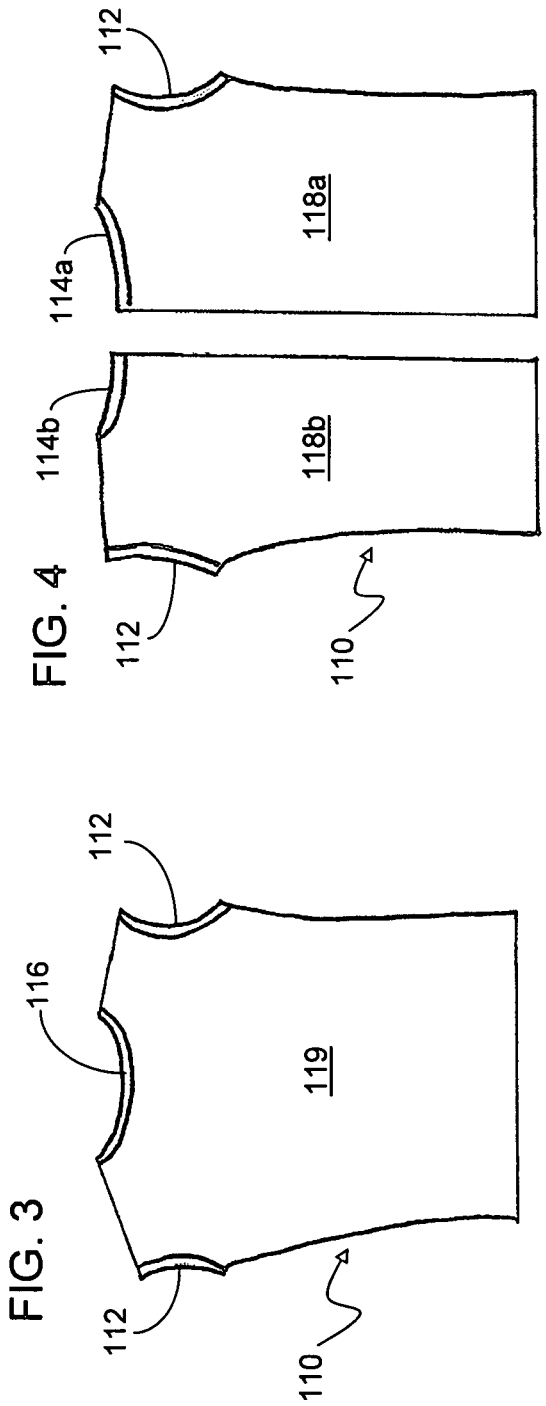

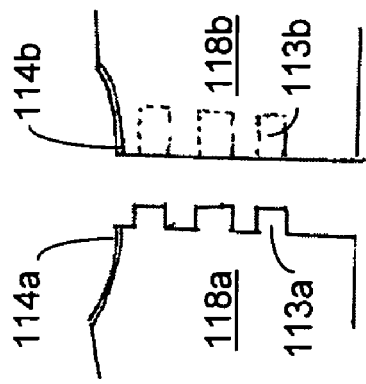
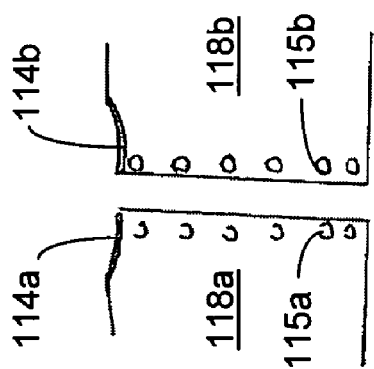
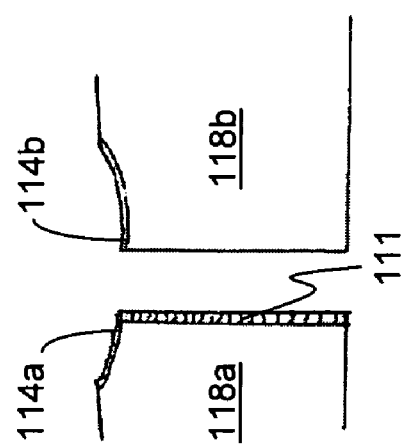

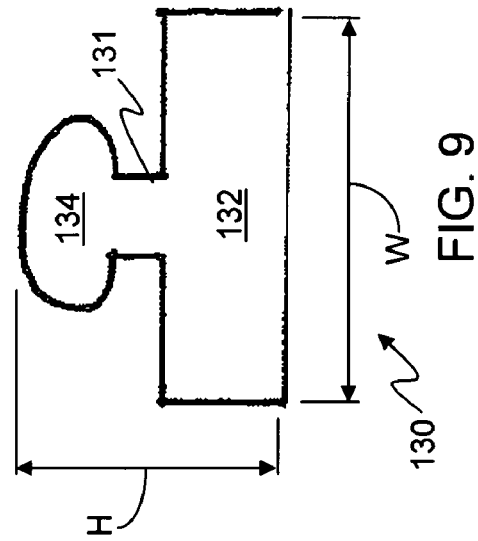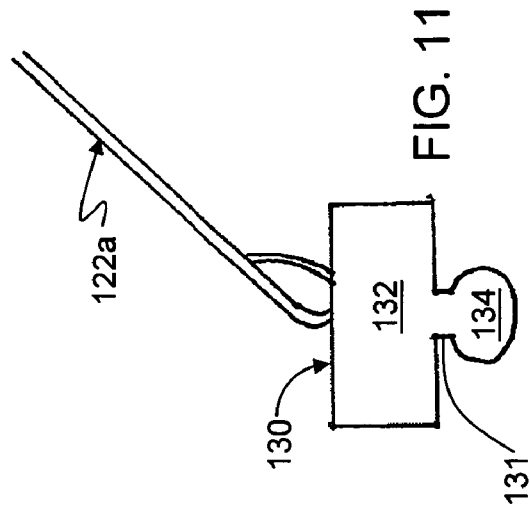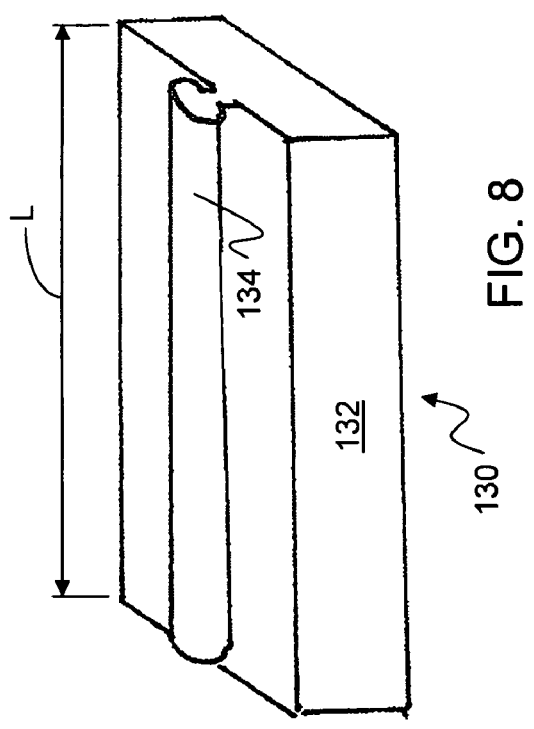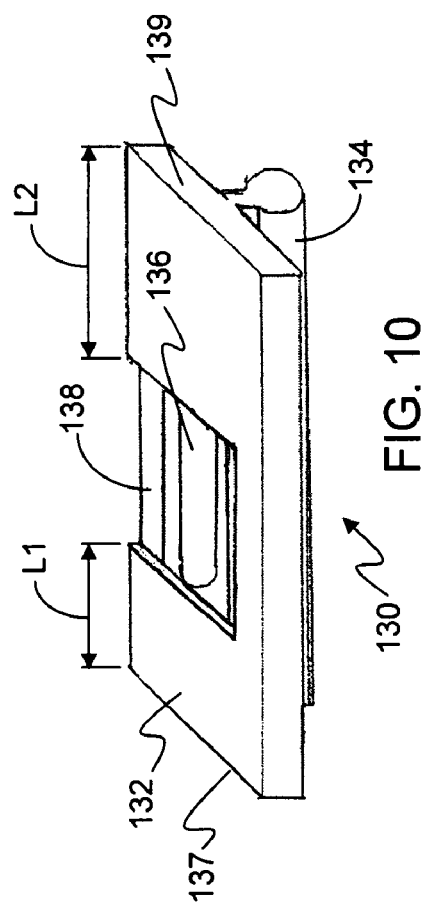

SAFETY GARMENT AND METHOD OF USING THE SAME

This application claims the benefit of U.S. Provisional Patent Application 60/921,903, filed Apr. 5, 2007, which is expressly incorporated by reference herein in its entirety.

FIELD OF THE INVENTION

The present invention relates to safety garments and devices.

BACKGROUND

A variety of restraint systems have been developed for children. For example, U.S. Pat. No. 5,263,725 to Wood describes a child restraint strap for a shopping cart.

The Consumer Product Safety Alert, concerning Shopping Cart Safety Alert, from the Consumer Product Safety Commission (CPSC #5075), indicates that an annual average of 21,600 children ages 5 years and under, are treated in U.S. hospital emergency rooms for falls from shopping carts during the years 1985-1996, including 22,200 falls in 1996 alone.

In July 2004, a voluntary standard for shopping carts was published to prevent falls. The American Society for Testing and Materials (ASTM) issued a voluntary standard, Standard Consumer Safety Performance Specification for Shopping Carts (F2372.04) addressing this fall risk. The Standard applies to children ages 6 months. (15 lbs+) up to 48 months (up to 35 lbs).

Improved safety devices for children are desired.

SUMMARY OF THE INVENTION

In some embodiments, a safety device, comprises a garment shaped to be worn on a torso of a user. A flexible strap is attachable to the garment and extending from the garment on first and second sides thereof, the strap having first and second ends. An elongated first fastener component is attached at or near the first end of the strap. The first fastener component has a longitudinal direction and is positionable in either a first orientation with the longitudinal direction of the first fastener component oblique or substantially normal to a portion of the strap at or near the first end thereof, or a second orientation with the longitudinal direction of the first fastener component aligned or nearly aligned with a portion of the strap at or near at the first end thereof. An elongated second fastener component is attached at or near the second end of the strap. The second fastener component has a longitudinal direction and is positionable in either a first orientation with the longitudinal direction of the first fastener component oblique or substantially normal to a portion of the strap at or near the second end thereof, or a second orientation with the longitudinal direction of the second fastener component aligned or nearly aligned with a portion of the strap at or near at the second end thereof. The first and second fastener components are capable of locking engagement with each other while joined in the first orientation, and are shaped for being used individually as anchors while in the first orientation and separated from each other.

In some embodiments, a method comprises: placing a garment on a torso of a user; providing a flexible strap attached to the garment, the strap having first and second ends extending from the garment on first and second sides thereof, the strap having an elongated first fastener component attached at or near the first end of the strap at an attachment location part way along a length of the first fastener component, the strap having an elongated second fastener component attached at or near the second end of the strap at an attachment location part way along a length of the second fastener component, wherein the first and second fastener components are capable of locking engagement with each other; inserting each of the first and second fastener components through respective first and second openings in at least one wall or frame of a vehicle in which the user is located, wherein each of the first and second fastener components has a length that is greater than a dimension of the first and second openings, respectively; and rotating the first and second fastener components to orientations substantially parallel to portions of the at least one wall or frame of the vehicle having the respective first and second openings, to anchor the first and second fastener components to the frame.

In some embodiments, a method comprises: placing a garment on a torso of a user; providing a flexible strap attached to the garment, the strap having first and second ends extending from the garment on first and second sides thereof, wherein the first and second fastener components are capable of locking engagement with each other; securing the user to a first object by joining the first and second fastener components to each other to form a closed loop for attachment to the first object; and anchoring the garment to walls or a frame of a second object by inserting the first and second fastener components through respective first and second apertures in the walls or frame of the second object, and positioning the first and second ends substantially parallel to the walls or frame having the apertures, the first and second fastener components being longer than a dimension of the apertures.

In some embodiments, a method comprises: placing a garment on a torso of a user; providing a first flexible strap attached to the garment, the first flexible strap having first and second ends extending from the garment on first and second sides thereof, wherein the first and second fastener components are capable of locking engagement with each other; securing the user to a first object by joining the first and second fastener components of the first strap to complementary first and second fastener components of a second strap, to form a closed loop for attachment to the first object; and anchoring the garment to walls or a frame of a second object while the user is not secured to the first object, by inserting the first and second fastener components through respective first and second apertures in the walls or frame of the second object, and positioning the first and second ends substantially parallel to the walls or frame having the apertures, the first and second fastener components being longer than a dimension of the apertures.

BRIEF DESCRIPTION OF THE DRAWINGS

FIG. 1 is a rear elevation view of an exemplary garment.

FIG. 2 is a rear elevation view of the vest shown in FIG. 1, in an unfolded position.

FIG. 3 is a rear elevation view of the vest shown in FIG. 1, as worn by a user.

FIG. 4 is a front elevation view of the vest shown in FIG. 1, as worn by a user.

FIGS. 5-7 are front elevation views showing various fastener options for the vest of FIG. 1.

FIG. 8 is a top isometric view of the male fastener component of FIG. 1

FIG. 9 is an end elevation view of the male fastener component of FIG. 1

FIG. 10 is a bottom isometric view of the male fastener component of FIG. 1

FIG. 11 is end elevation view of the male fastener component of FIG. 9, with a strap attached.

DETAILED DESCRIPTION

Figure 13:
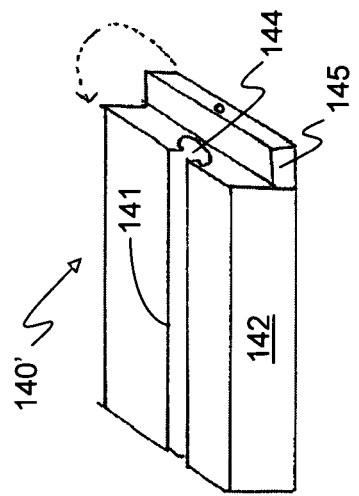
FIG. 13 is a variation of the female fastener component of FIG. 12.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Vest

Figure 20:
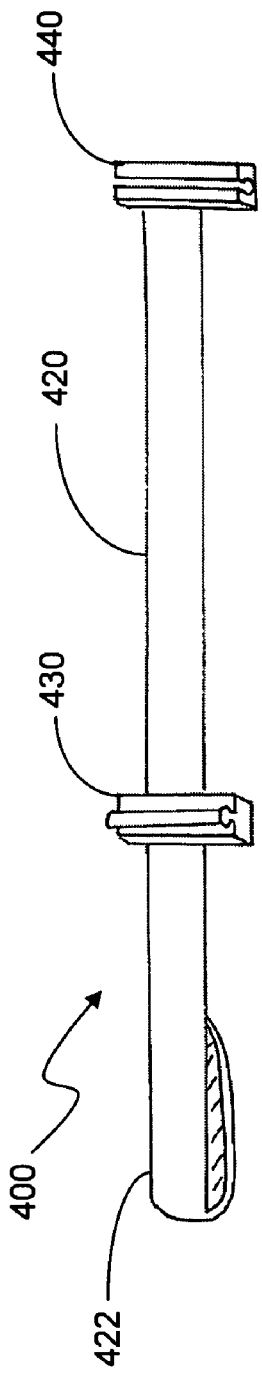
FIG. 20 is a front view of an extension strap suitable for attachment to the garment of FIG. 1.

FIG. 1 shows a safety garment 100. The exemplary garment 100 includes a child safety vest 110, which limits the upward and lateral movement of a child, thereby restraining a child safely and comfortably while seated in a household or restaurant high chair 300 (shown in FIG. 21) and also shopping carts 200 (shown in FIGS. 16-19 and 23). The vest 110 can also be utilized as a part of a tether system for ambulatory children when a separate attachment strap 440 (as shown in FIGS. 20 and 24) is used.

FIGS. 1-7 show one embodiment of the safety garment 100. The exemplary safety garment 100 is a child safety vest, which may be manufactured in different sizes to fit children of ages six months to four years. Although the example described below includes a vest 110, the garment 100 is not limited to vests, and may alternatively take the form of a jacket, coat, shirt, jump suit, or harness system.

The garment 100 is preferably made of a lightweight, durable water repellant material. The garment 100 may include a vest 110 having a contoured neck 114a, 114b, 116 with a midline zipper closure 111 (FIG. 5) on sides 118a and 118b, allowing the garment to be placed on the child with the closure facing towards the child's front or back. In alternative embodiments, the zipper 111 is replaced by hook 113a and loop 113b closures (FIG. 6) or buttons or snaps 115a, 115b (FIG. 7), or ties (not shown).

A strap 120 of a durable material, such as nylon or polyester, is sewn across the face 119 of the vest 110 opposite the closure 111, to run parallel to the bottom edge of the vest 110, and about four to about eight inches (preferably about six inches) above the bottom edge of the vest. The strap 120 extends out from the vest 110 on each side and may optionally have a sliding tightener 150 on each side, allowing both attached strap extensions 122a, 122b to vary in lengths from about nine inches to about 17 inches, preferably from about 11 inches to about 13 inches. In some embodiments, the length of the strap 120 is made short enough so that the child cannot trip over straps 122a, 122b while walking, even if the strap extensions 122a, 122b are hanging freely. Both attachment strap extensions 122a, 122b are also equipped with a locking fastener system 130, 140 described below.

In some embodiments, the vest 110 has at least two layers of material, preferably keeping the combination soft and flexible. In some embodiments, absorbent material is used on the outside, and an inner layer composed of water repellant material. The absorbent outer layer serves as a bib which the child cannot remove. In some embodiments, an absorbent bib panel is provided in the front of the vest 110 at or near its top, while the remainder of the garment 100 may have a moisture repellant outer fabric material layer. In other embodiments, the outer layer is water repellant, and an absorbent or insulating material is included in the inner layer.

The garment 100 may be provided in two forms, both a durable and a disposable form. Both could be used for the purposes of advertising by printing logos 102 etc. on the face of the vest itself, as shown in FIG. 1.

Either the inner or outer layer may be made of a soft, absorbent material, such as cotton or a polyester/cotton blend, and the inner layer composed of a water-repellant material, such as nylon, polyester or polypropylene, and may be a solid fabric or an open net or mesh. Preferably, the material is lightweight, durable and breathable. It may be worn by children in hot weather as well as washed multiple times, for example, due to food/fluid spills. The vest can preferably be placed on a child ahead of time (before fastening the child to a chair or shopping cart), but this is not a requirement. As many children snack while out and about, this will protect the clothes worn underneath.

Shape: In some embodiments, the shape of the vest 110 may be as such, a blank side 119 with a contoured neckline 116 and armhole borders 112, allowing for a sleeveless opening. It will cover the upper torso and may end distally with a straight edge border at the waistline. The size of 119 will be relative to the sizing chart, whether it be for an infant, 2T, 3T or 4T size. In some embodiments, the armholes 112 may have a means for attaching sleeves.

The opposing side may be made up of two half panels 118a, 118b, allowing for a midline opening. Again, the borders of this side 118a, 118b will allow for a contoured neckline 114a, 114b and sleeveless arm openings 112 on either side. The vest 110 can be manufactured so that each half panel of 118a, 118b will be sewn on either side of Side 119 or could be manufactured as one piece, depending on manufacturing preference.

The contoured neckline 114a, 114b, 116 allows the midline opening to be placed posteriorly or anteriorly, for reasons explained below.

Strap

A length of strap 120 (which may be, for example, a webbing), may be formed from a length of cotton, nylon, or polyester material, but is not limited thereto. The strap 120, is attached to vest 110 and reinforced by stitching parallel to and about 6" above the bottom border of side 119. In some embodiments, a ¾" webbing is used to form the strap 120, keeping the garment 100 lightweight but durable, to reduce bulk and weight of the end product. The strap may be placed 6" above the bottom border of the vest to decrease the child's leverage in shopping carts 200 and high chairs 300.

The strap 120 may be stitched to side 119 only, as one continuous piece, having extensions 122a, 122b extending out about 12" to about 13" on either side of the vest 110. Both lateral strap extensions 122a, 122b may be fitted with a sliding buckle 150, allowing the strap extensions 122a, 122b to be shortened or lengthened. Both strap extensions 122a, 122b would also be fitted at their respective end points with a fastener or clasp component, comprised of a male fastener component 130 and a female fastener component 140, described below.

For typical infant sizes, these strap lengths should allow for a 11-13" maximum extension, but are not limited to this length. One advantage to keeping the lengths as short as possible is to limit the risk of a child tripping or inadvertently becoming tangled up on an object, causing harm, while the male and female fastener components 130, 140 are not locked together.

Fastener System

Preferred embodiments include a safe, convenient fastener 130, 140, making the garment 100 extremely versatile.

FIGS. 8-15 show an exemplary fastener system. FIGS. 8-11 are different views showing the male fastener component 130, and FIGS. 12-15 show the corresponding female fastener component 140. The locking fastener (e.g., buckle or clasp) system 130, 140 may be made of a strong, hard plastic. The exemplary fastener has a male component 130 and female component 140 which slide together to form a lock. The male component 130 has a solid, cylindrical tube 134 which runs along the undersurface of the body 132 of the male component.

The cylindrical tube 134 of the male fastener component 130 has a member 131 supporting the cylinder 134, and the casing 144 of the female fastener component 140 has a corresponding groove 141 along their entire lengths which may be aligned to allow the tube 134 of male fastener component 130 to enter the casing 144 of the female fastener component 140.

Each of the male and female fastener components 130, 140 should have a length that is longer than a smaller dimension of the openings 202 of a frame of a shopping cart 200 (FIGS. 16-19), and a width W and height H that are smaller than the smaller dimension of the openings 202. This will ensure that the male and female fastener components 130, 140 can be inserted through the opening 202, and can subsequently act as anchors when rotated.

In some embodiments, the dimensions of the male component 130 are about ¾" or less in width W (preferably from about ⅝" to about ¾") and about ¾" or less in height H (preferably from about ⅝" to about ¾"). The length L of the male component 130 can vary in range between about 2" and about 3½". In some embodiments, the body 132 of the male component is rectangular in shape and incorporates a raised, solid cylindrical tube or projection 134 which runs medially, along the length of the rectangular body 132.

The male fastener component 130 should be manufactured without seams to increase strength.

Referring again to FIGS. 12-15, the female fastener component 140 may have a concave shaped casing 144, which accepts the cylindrical tube 134 of the male fastener component 130, allowing tube 134 to slide the entire length of the casing 144 of the female fastener component 140. The female casing 144 has an end cap (not shown) at trailing end 147 and a retaining means 143 (FIG. 12) or 145 (FIG. 13) at the leading end 149, which prevents the leading end 139 of the male component 134 from sliding out of the casing 144 of the female fastener component 140 and disengaging.

The female fastener component 140 of the system should have dimensions of about ¾" or less in width W and ¾" or less in height H. Similarly, the length L of the female fastener component 140 can vary in range between about 2 and about 3½", but of a length which should match the male fastener component 130. The rectangular body 142 of the female fastener component 140 should incorporate a recessed channel 144 along the midline of the body, which may include a cap or fixed wall at one end. The dimensions of the male and female fastener components 130, 140 should compliment each other, allowing the cylindrical projection 134 of the male fastener component 130 to slide along the recessed channel 144 of the female fastener component 140. The cap (item 143 in FIG. 12 or item 145 in FIG. 13) at one end 149, prevents the male fastener component 130 from passing completely through the recess 144, effectively locking the fastener system together. The size of the cylinder 134 and recessed channel 144 should be large enough to allow this union, keeping within the ¾" height.

Figure 12:
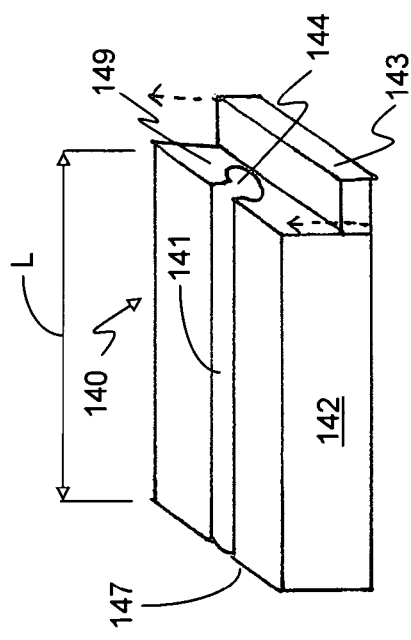
FIG. 12 is a top isometric view of the female fastener component of FIG. 1

FIGS. 12 and 13 show two versions of the female fastener component. In FIG. 12, the female fastener component 140 has a sliding end cap 143. The end cap 143 (FIG. 12) slides over the end of the opening 144, to lock the male and female fastener components together, and may have a detent (not shown) to retain the end cap 143 in place. In FIG. 13, the female fastener component 140' has a pivoting end cap 145. The end cap 145 (FIG. 13) pivots over the end of the opening 144, to lock the male and female fastener components together, and may have a living hinge to connect the end cap 145 to the female fastener component 140.

Figure 25:
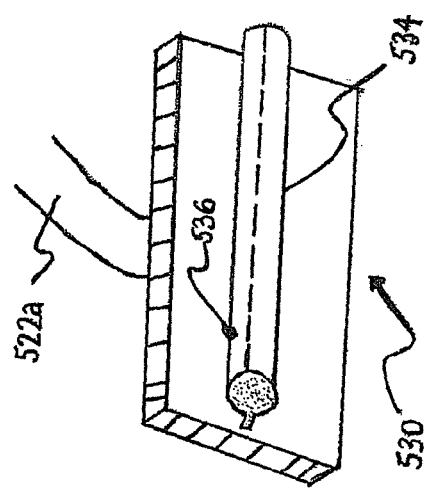
FIGS. 25 and 26 show alternative fastener components suitable for use in the garment of FIG. 1.
Figure 26:
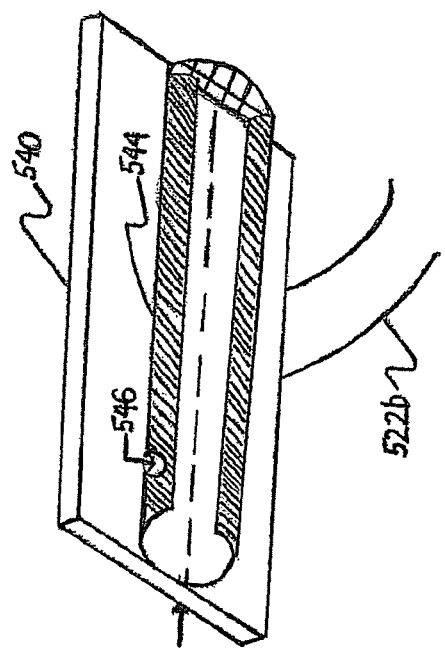

Referring now to FIGS. 25 and 26, in some embodiments of the male fastener component 530, about ⅔ of the length away from the end of the cylinder 534, a spring-loaded nipple or protuberance 536 (FIG. 25) may optionally be provided to lock the male 530 and female 540 fastener components together.

Located about ⅔ of the length away from the receiving end of the casing 544 of the female fastener component 540, an optional hole 546 (FIG. 26) will accept the spring-loaded nipple 536 projecting from the side of the tube 534 of male fastener component 530. By sliding the male and female fastener components 530, 540 completely together, the spring-loaded nipple 536 on the male component 530 will protrude through the hole 546 in the casing 544 of the female fastener component 540, thus locking the system. The system 530, 540 is unlocked by depressing the nipple and sliding the components apart.

The male and female fastener components 130, 140 of the fastener system, to be referred to as the fastener for brevity, should be made of a durable, hard material, possibly of a plastic such as polyvinyl chloride (PVC), chlorinated polyvinyl chloride (CPVC), polyethylene, polybutylene, acrylonitrile butadiene styrene (ABS), polystyrene, polyamide, or polypropylene, but is not limited thereto. In some embodiments, one or more reinforcing members (not shown) are included with the fastener componenets 130, 140. For example, a plurality of metal (e.g., aluminum) reinforcing rods may be embedded within the fastener components.

The fastener 130, 140 could be further locked together using additional means. A compact, locking mechanism could be secured to the receiving end of the female fastener component 140. The fastener 130, 140 would be joined together by sliding the cylinder 134 of the male fastener component along the recessed channel 144 of the female fastener component 140, until it lines up with the capped end 147 of the female fastener component 140. The compact locking mechanism 143 or 145 would then twist or slide up, securing the fastener 130, 140 as shown in FIGS. 12 and 13.

Figure 14:
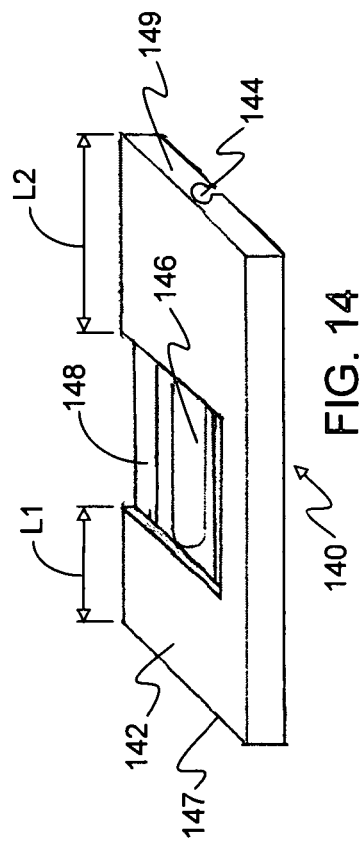
FIG. 14 is a bottom isometric view of the female fastener component of FIG. 1
Figures 16, 17:
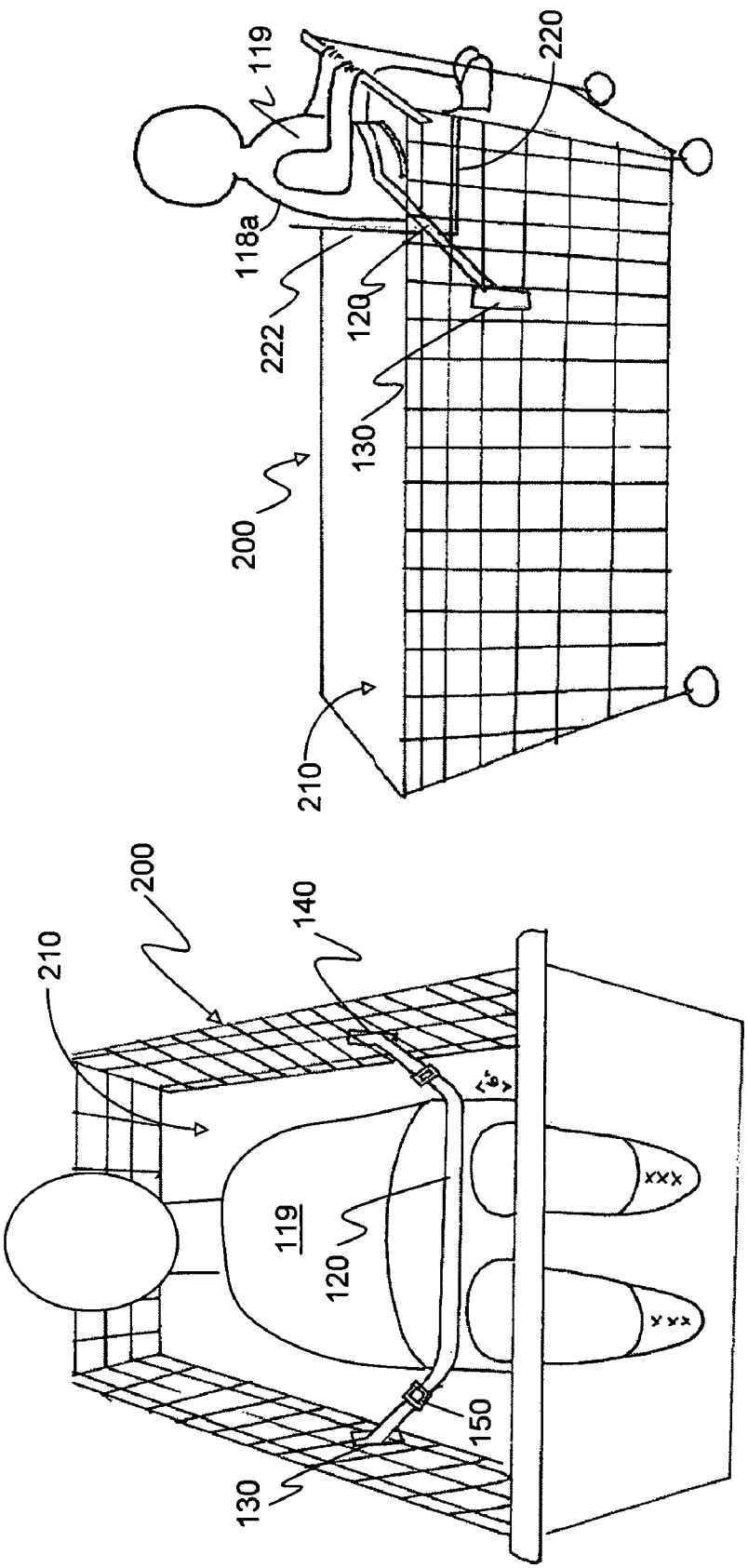
FIGS. 16 and 17 are rear and side views of a child secured to a shopping cart by the garment of FIG. 1.
Figure 18:
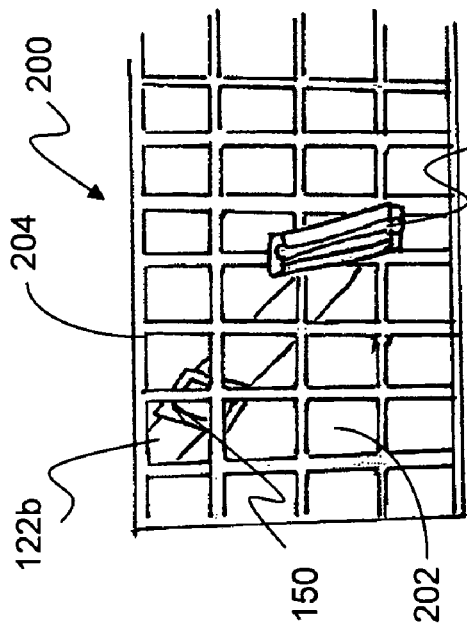
FIGS. 18 and 19 show the male and female fastener components of FIG. 1 being used to anchor the child to the walls of the shopping cart.
Figure 19:
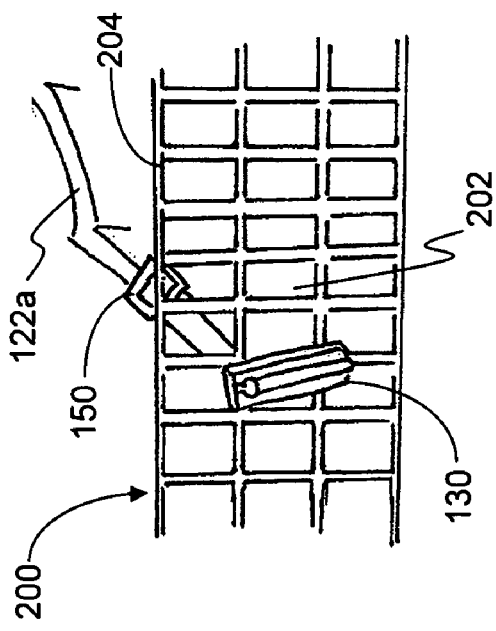

As best seen in FIGS. 10 and 14, each of the male and female fastener components 130, 140 has a bar or member 136, 146 to which the ends of strap 120 are attached. In some embodiments, it is advantageous to recess the members 136, 146 on the back sides of the male and female fastener components 130, 140, to which the extension straps 122a, 122b are attached. In some embodiments, the rear surfaces of the male and female fastener components 130, 140 have a shallow recess 138, 148 on one side, against which the strap 120 can lay flat when inserting the fastener components 130, 140 through the openings in the wall or frame of the shopping cart 200. This allows the overall width W and height H of the fastener components 130, 140 to be as large as possible (for increased durability) while still being capable of fitting through the openings 202 in the shopping cart 200. The strap 120, which may be about ¾" wide, loops around a plastic bar or member 136, 146 running across the recessed attachment point. By recessing the loop of strap 120, the height H of the male and female fastener components 130, 140 can be maintained within a desired size (e.g., ¾") that permits the male and female fastener components 130, 140 to be inserted through an opening 202 in the side wall 204 or frame of a shopping cart 200 (best seen in FIGS. 18 and 19).

Figure 15:
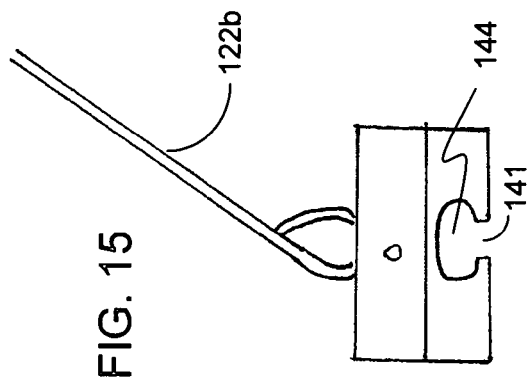
FIG. 15 is end elevation view of the female fastener component of FIG. 9, with a strap attached.

FIGS. 11 and 15 are side elevation views showing how the recessed attachment members 136 (FIG. 10) and 146 (FIG. 14) in male/female components 130, 140, respectively, allow the strap extensions 122a and 122b to loop onto themselves and form connections.

The garment 100 is designed to keep children safe and seated in all restaurant/domestic highchairs 300 and all shopping carts 200. It may also be used in other types of seats and other types of vehicles, such as a toy wagon or tricycle. In some embodiments, the garment 100 also serves as a tether by utilizing the looped end 422 of the extension strap 420 and also acts as a bib. Some embodiments include a means of carrying contact and identity information hidden on the inside, which can be of assistance should a child get lost while wearing the garment. The garment 100 may also be used as an advertising tool for retailers who can print their logo 102 on the front or rear (or other regions) of the vest 110 itself.

In some embodiments, there is an advantage to keeping the recessed attachment members 136, 146 for the strap extensions 122a, 122b closer to the bottom of the fastener components 130, 140 than the top. For example, in FIGS. 10 and 14, the recessed attachment members are positioned at a distance L1 from the trailing end 137, 147 of the fastener components 130, 140, and at a distance L2 from the ends 139, 149, where L2 is greater than L1.

When manufacturing the male fastener component 130 of the buckling system, grippers should be placed on the looping bar 136 of the recessed attachment point. This way, when a male fastener component 130 is placed on one end of the "separate attachment strap" 420, it can slide along the length of the strap 420, yet anchor at a suitable spot when desired. This allows for the different extension points for use with all types of domestic and restaurant highchairs 300.

Although an exemplary fastener system is described above, other types of fastener systems may be substituted, having two corresponding components capable of locking engagement with each other, each capable of passing through and opening in a wall of a shopping cart, and of being placed in an anchoring position.

Figure 27:
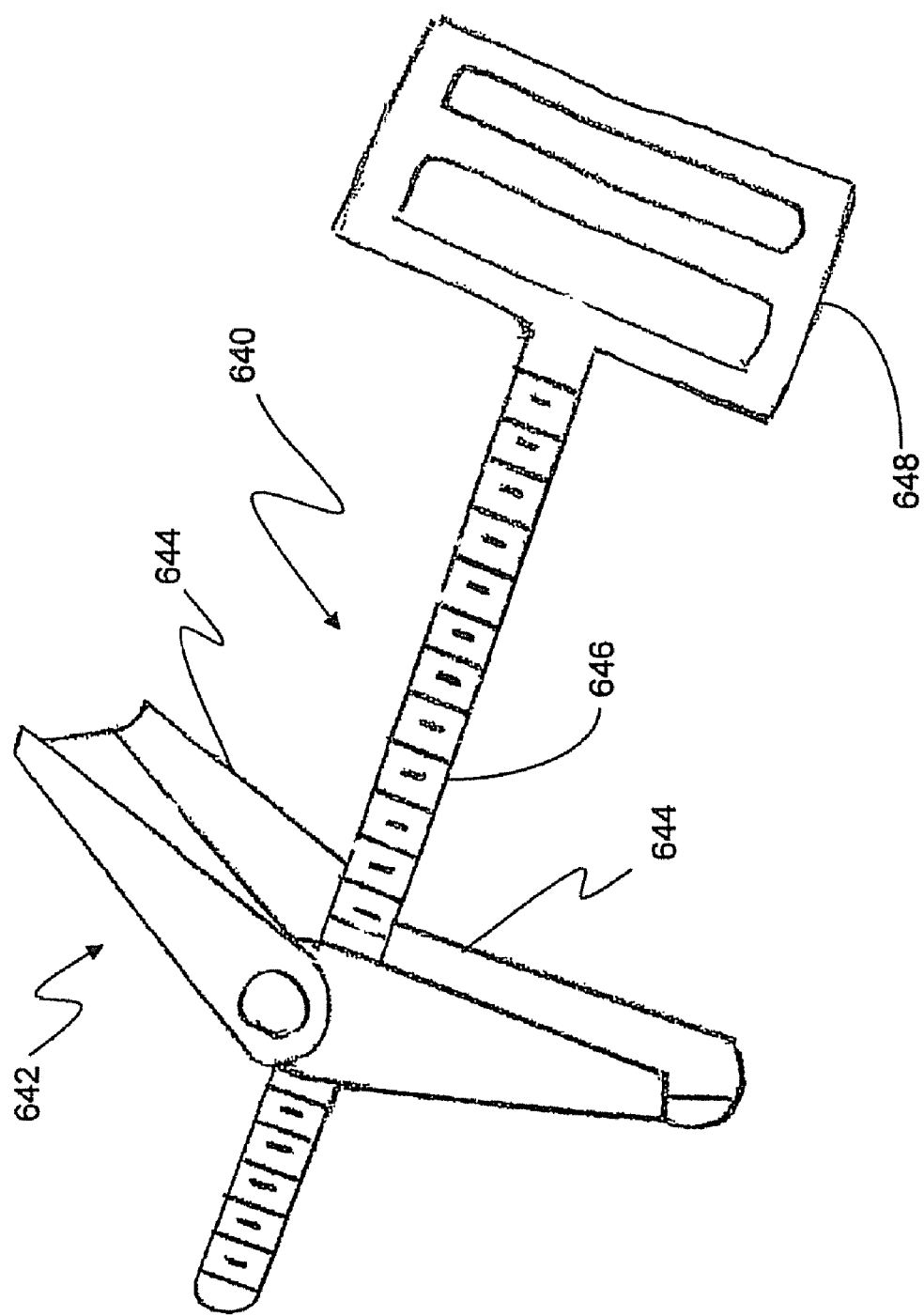
FIG. 27 shows an alternative anchoring device that can be attached the ends of the strap shown in FIG. 1.

For example, FIG. 27 shows one alternative toggle-type anchor 640 that may be used for the shopping cart application, instead of male and female fastener components. The anchor 640 includes a toggle mechanism 642 having two spring mounted pivoting arms 644, which are biased by a spring (not shown) towards the open position as shown. The arms 644 can be folded down manually during insertion through the shopping cart openings 202, and then released to return to the open position. The toggle mechanism 642 is connected by a member 646 to a sliding fastener 648, to which strap extension 122a, 122b may be connected. Although two anchor components 640 as shown in FIG. 27 are not adapted to be locked together to secure the child in a chair, other embodiments are contemplated in which two different toggle anchors are used, which are capable of locking to each other to secure the child in a chair, and also capable of providing the toggle function for anchoring the child to a shopping cart.

Separate Attachment Strap Assembly

Referring now to FIG. 20, a nylon extension strap assembly 400 has a strap 420 with a fixed fastener component (e.g., a female fastener component 440) at one end. The extension strap 400 may have any of a variety of lengths, such as about two feet, about three feet, about four feet or about six feet. A corresponding fastener component (e.g., a male fastener component 430) capable of mating with the fixed fastener component 440 is included. In some embodiments, the male fastener component 430 can move and secure itself at any point along the extension strap. This allows the male and female components 430, 440 to be set apart at varying distances. At the end 422 near the male fastener component 430, the strap 420 folds back upon itself to form a loop. In other embodiments, the male component is fixed, and the female component is movable.

Figure 21:
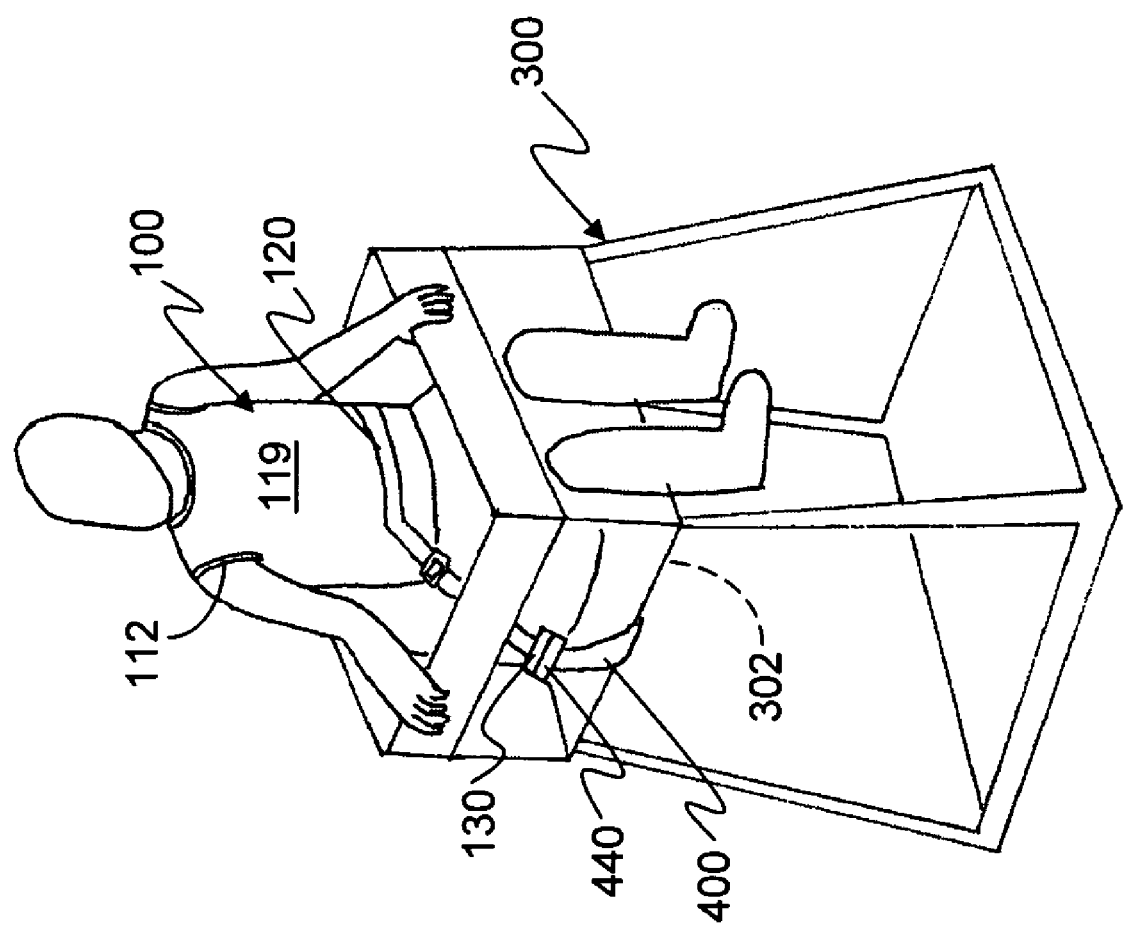
FIG. 21 is an isometric view of a child secured to a high chair using the garment of FIG. 1.

FIGS. 20, 21 and 24 show the separate attachment strap assembly 400 that can be used in combination with the garment 100, for securing a child to a seat 300 (FIG. 21), or to form a secure tether for the garment 100 (FIG. 24). The attachment strap assembly 400 includes an attachment strap 420 and fastener components 430, 440 described below. The use of a separate attachment strap 420 made out of the same material as strap 120 (webbing or other strong, flexible material) can greatly increase the versatility of the vest 110. The strap 420 can vary in lengths from about 35 inches to about 45 inches but not limited to this range. On one side, there should be a fixed (e.g. female) fastener component 440 substantially the same dimensions and shape as female fastener component 140. At the opposite end, the attachment strap 420 should loop upon itself to form a handle 422, allowing an adult's hand to grasp the strap 420 more securely. A mating (e.g., male) component 430 should be attached at or near this end, optionally using a recessed attachment member similar to member 136 shown in FIG. 10. In some embodiments, the male component is free to slide along the length of the attachment strap.

Following are non-limiting examples of uses for this same attachment strap assembly 400:

1. A child wearing the vest 110 can be placed in a domestic or restaurant highchair 300, of any make or type (as shown in FIG. 21). The female fastener component 440 of the separate attachment strap 420 may be locked together with the male fastener component 130 of the child's garment 100. The separate attachment strap 420 would then be placed to run along the undersurface of the seat 302 of the highchair 300. The male fastener component 430 of the attachment strap 420 would then lock with the female fastener component 140 of the child's vest 100. The attachment strap 420 would now be shortened using the sliding male fastener component 430, such that the child is secured in a sitting position.

Figure 22:
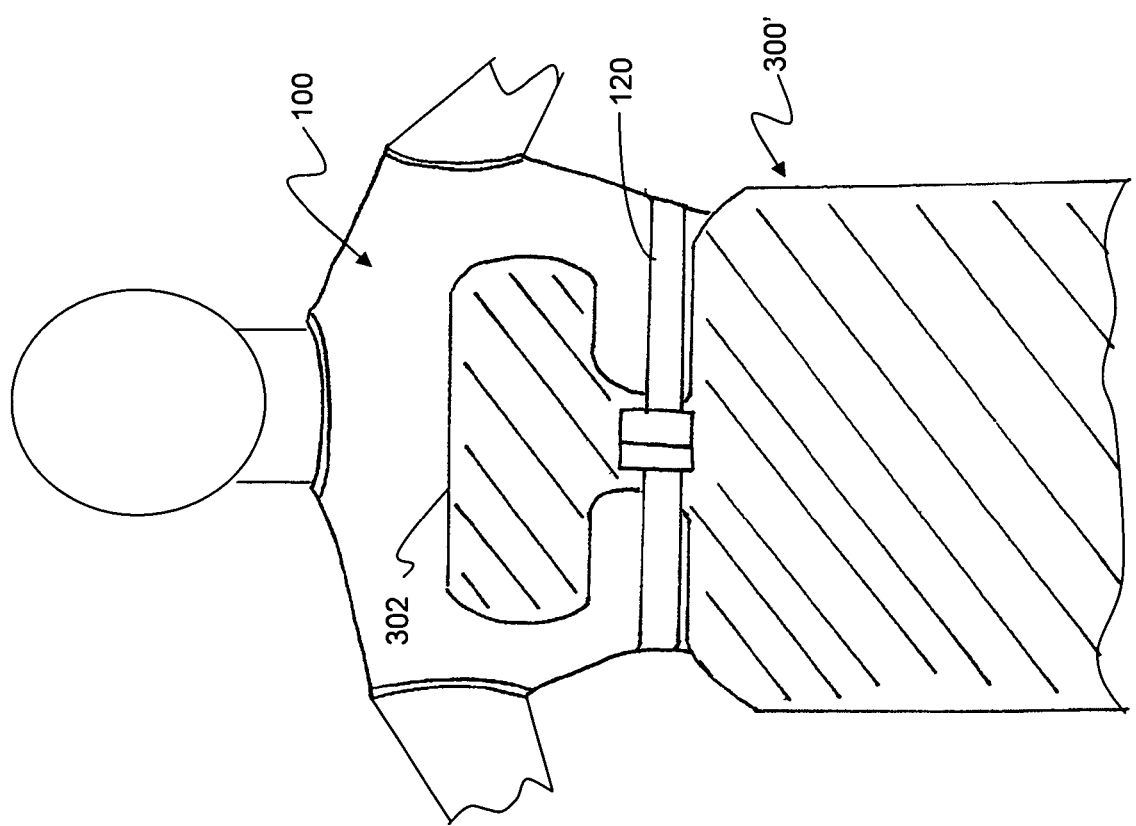
FIG. 22 shows a rear view of a child secured in a plastic, molded high chair using the garment of FIG. 1.

As shown in FIG. 22, the vest's restraining system can be used for older highchairs 300' only fitted with lap belts (not shown). The male and female fastener components 130, 140 connect directly to each other to secure the child to the back of the chair 300', below the head rest, and the strap 420 is not needed. Also, having the benefit of an unmovable absorbant vest front—which the child cannot pull off—in place, caregivers may opt to use the vest 110 regardless of the presence of an available restraint system on the chair 300, due to the advantage of protecting their child's clothes during mealtime.

Some types of plastic restaurant highchairs are molded such that the outer surface of the seat is rounded. For these chairs, the backrest of the child's seat typically have contoured edges, allowing the extension straps 122a, 122b of the vest 100 itself to lock in place behind the seat. This provides an alternative securing method that can also be used in any type of seat that does not easily lend itself to wrapping the extension straps 122a, 122b around the bottom of the seat.

Placing the strap 120 about 6" above the bottom edge of the vest 110, positions it to be approximately level with the top of the seat 220 of a shopping cart or seat 302 of a highchair 300, decreasing the child's leverage and ability to stand.

2. As shown in FIG. 24, the looped ending 422 of the separate attachment strap 420 can expand the use of the garment 100 to also serve as a tether. An optional additional male fastener component 130' can be attached to Side 118a, 118b of the vest 110 for this purpose. This should be in a mid scapular region and to one side of the midline closure for best ease of use and caregiver control. The additional male fastener component 130' may be configured similarly to male fastener component 130, as described above. By locking the female fastener component 440 of the separate attachment strap 420 to this male fastener component 130' on side 118a, 118b of the vest 110, a tether is formed. (Alternatively, the female fastener component 440 of the separate attachment strap 420 can be attached to the male fastener component 130 on strap extension 122a.) The adult then holds the loop 422 of the now connected "separate" attachment strap 420. The garment 100 may be placed on the child before leaving home, making it a routine for the child, decreasing the reluctance to wear the vest 110 while out running errands or eating. Preferably, the fastener components 130, 140 are sized at a minimum size consistent with anchoring the strap extensions 122a, 122b to the type of shopping cart 200 in which the garment 100 is to be used, to decrease bulk without decreasing durability or function. Thus, if shopping carts 200 are developed having openings of a new size, one of ordinary skill can readily adapt the size of the male and female fastener components 130, 140 consistent with the teachings provided herein. The fastener components 130, 140 can be locked together behind the child when not in use, avoiding tripping.

The exemplary vest 110 and safety system 100 can be used for all shopping carts 200, domestic and restaurant highchairs 300, as a tether and as a secure bib.

Operation

FIGS. 16-19 show the garment vest being used to secure a child in a seat 220 of a shopping cart 200. For ease of viewing in FIGS. 16 and 17, portions of the vest 110 are omitted from these two figures, but are understood to be present. For use as an anchor on typical shopping carts 200, the length of each fastener component 130, 140 should include a length L2 of ¾" or more above the attachment member 136, 146 and a length L1 of ½" or more below the attachment member. When the fastener components 130, 140 are anchored against side walls 204 of the shopping cart 200, the fastener components 130, 140 tend to align themselves, so that projections of the fastener components 130, 140 and the strap 120 along the side wall of the cart are substantially parallel to each other. In the discussion below, the term "superior end" refers to the larger end 139, 149 of each fastener component 130, 140 that is inserted through the opening 202 in the shopping cart 200 first (the leading end). The "inferior end" 137 is the smaller end inserted through the opening 202 last (the trailing end). When the fastener components 130, 140 are anchored, the superior end 139 is oriented in the distal direction, facing away from the child, and the "inferior" end 137, 147 faces the proximal direction approximately toward the child. More specifically, when anchored, the projections of the fastener components on the walls of the cart will be substantially aligned with the inferior end 137, 147 pointing towards the child, and the superior end 139, 149 pointing away from the child.

Referring now to FIGS. 16-19, when used in shopping carts 200, the vest 110 is preferably placed on the child with the zipper 111 opening to the rear of the child. The attachment straps 122a, 122b of the vest 110 are extended in length so that the fastener components 130, 140 on either side can be inserted through respective openings 202 of the crisscross framework 204 on each side of the shopping cart 200. Preferably, the male and female fastener components 130, 140 are to be inserted fully through openings 202 which are located behind and approximately 4 inches below the level of the seat on which the child is sitting. This locates the fastener components 130, 140 out of reach of the child, so that the child cannot let himself or herself out. Once one of the fastener components 130, 140 fits entirely through the opening 202, the fastener component is then turned so that it wedges against the outer surface of the shopping cart 200, forming an anchor. The same process is then repeated on the other side of the cart. The system is secured by using the sliding tighteners 150 on both attachment straps 122a, 122b.

In some embodiments of the method, the fastener components 130, 140 can both be anchored on the same side wall 204 of the shopping cart 200; or one fastener component can be anchored to a side wall while the other fastener component is anchored to the floor of the cart; or both fastener components can be anchored to the floor or front of the basket of the cart. However, it is believed to be preferable to anchor the fastener components on respective side walls.

It is preferred to provide a longer length L2 for anchorage of the superior end 139, 149 of each fastener component 130, 140 for attaching the system to the frame of a metal cart 200. The crisscross framework of the cart 200 is so narrow that, if the attachment member 136, 146 for the strap is medially placed along the length of the fastener components 130, 140, there is a risk of the fastener components 130, 140 pulling free. The inferior end 137, 147 of the fastener component 130, 140 anchors easily against the wall/wire when the strap extension 122a, 122b is pulled, however providing the ½" extra length (L2−L1) superiorly ensures that the superior end 139, 149 anchors against the adjacent bar of the cart frame 200, as most metal carts have openings that are ¾-1¼" plus wide.

The width W and height H of the male/female fastener components 130, 140 are selected to be below a predetermined value. The extensions straps 122a, 122b of the webbing can be lengthened using the sliding fastener 150. This enables their end points to reach areas on either side of the basket 210 of the shopping cart which are behind and below the levels of the seat 220 in which the child is sitting, usually 10-11" away from the vest 110 itself. On one side, the male fastener component 130 is fed through an opening of the crisscross framework. On the other side, the female fastener component 140 is also fed through an opening in the crisscross framework, behind and below the level of the child's seat 220 within the shopping cart 200.

A caregiver places a child in the collapsible seat 220 of the shopping cart 200. The vest 110, optimally in this situation, is worn such that sides 118a, 118b is facing posteriorly. The strap extensions 122a, 122b, extending from side 119 are lengthened using the sliding buckles 150. The respective ends with the male and female fastener components 130 and 140 are fed through the grid backrest 222 of the child's seat 220 and directed to an area of the inner wall 204 on either side of basket 210. The male fastener component 130, attached to the extension 122a of strap 120, is directed through a hole 202 in the inner surface of the basket 210 of the cart, at a point behind and below the level of the child's seat 220. After inserting the male fastener component 130 through the hole 202, and pushing the component 130 through the hole 202 in its entirety, component 130 is then turned and anchored against the outer wall of the cart's basket 210. The same steps are performed for the female fastener component 140 so the two sides are balanced. The system is secured by shortening the lengths of the strap extensions 122a, 122b, such that a child's upward and lateral movement is limited. This prevents a child from standing up or leaning over in the cart, decreasing the risk of fall or tippage.

The vest 110 may be placed on a child with the midline opening of side 118a, 118b, facing posteriorly, and the side 119 on the child's front. This limits the child's ability to reach back and remove the vest 110. In some embodiments, a hook and eye may optionally be added to the top of vest 110 (e.g., those suited for 3T and 4T sizes), to further limit a child with improving dexterity to remove the vest.

Also, by placing the vest 110 in the above-described position, the strap 120 stitched to side 119, is under less stress and tension, as the length of strap 120 is aligned: from the fastener component 130 anchored on one side of the cart, through the back of the child's seat 220, around the anterior waist of the child, through the back of the seat on the opposite side and anchored by fastener component 140 on the opposite side of the cart's framework. It is one continuous curve. The downward pull of the anchoring male and female fastener components 130, 140 keeps the child seated. If the child strains against the strap 120, there is no tendency to pull the garment 110 away from the strap 120 (because the child would be pushing the side 119 of the vest against the strap 120). This means that the overall integrity of the system is not limited by the integrity of the joint between the strap 120 and the garment 100, but only by the strength of the strap 120 and the male and female fastener components 130, 140.

FIG. 21 shows the garment being 100 used to secure a child in a high chair 300. Children are placed approximately 6" into the seats 300 of these equipment. This means the level of the strap 120 is close to being flush with the upper boundaries of these seats. This decreases the amount of leverage a child can use to raise their body, reducing the chance of the child freeing himself or herself.

In a highchair 300, the child wearing the garment 100 is placed in the seat with the zipper closure 111 to the front or back. FIG. 21 shows the garment 100 with the zipper facing the back (not visible in FIG. 4). The extension strap assembly 400 is placed along the undersurface of the highchair's seat and the strap 420 comes up along each side of the seat so that the appropriate component of the extension strap's locking fastener slides in place with the corresponding locking component of the garment 100 (male to female). FIG. 21 only shows the male fastener component 130 of the garment connected to the female fastener component 440 of the extension strap assembly 400. The female fastener component 140 of the garment 100 is connected to the male fastener component 430 of the extension strap assembly 400 in a similar manner on the other side of the chair (not shown in FIG. 21). The system is secured by tightening the movable (e.g., male) fastener component 430 of the extension strap 420. The sliding tighteners 150 of the attachment straps 122a, 122b of the vest 110 can also be shortened if desired.

Because of the configurations of high chairs, booster seats and other chairs vary, the garment 100 may be used to secure the child by wrapping the extension straps 122a, 122b and/or the attachment strap assembly 400 around, under or through the seat to provide appropriate locking engagement while securing the child.

Other Variations

The design of the vest, shirt, coat, jacket component 110 of garment 100 allows for it to be made in a disposable form. The separate attachment strap 420 could continue to be used repeatedly with different types of garments 100 and/or differently sized garments, as the child grows.

Figure 23B:
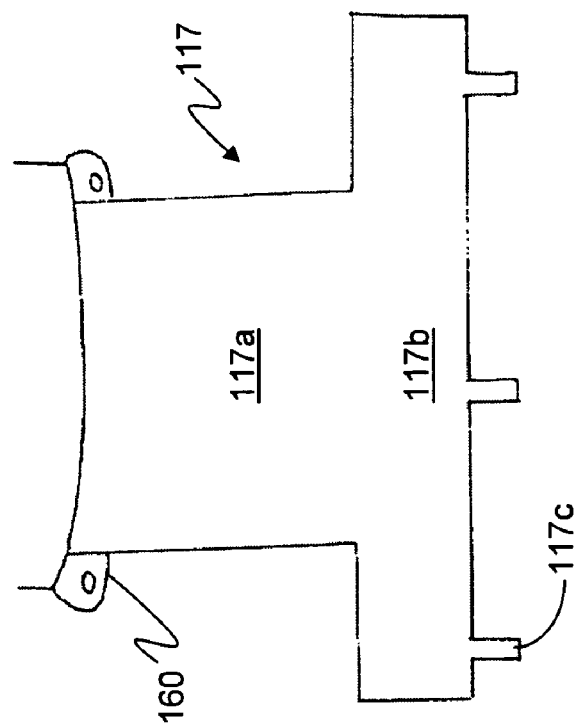
FIGS. 23A-23C shows an optional stowable hygienic lap panel, which can be attached to a portion of the shopping cart or high chair.
Figure 23A:
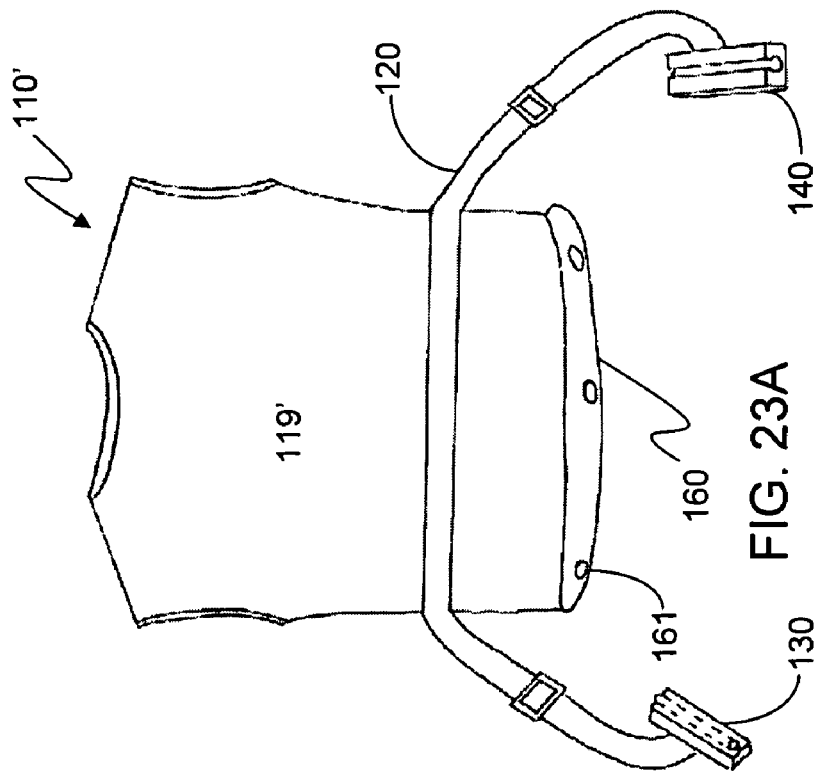
Figure 23C:
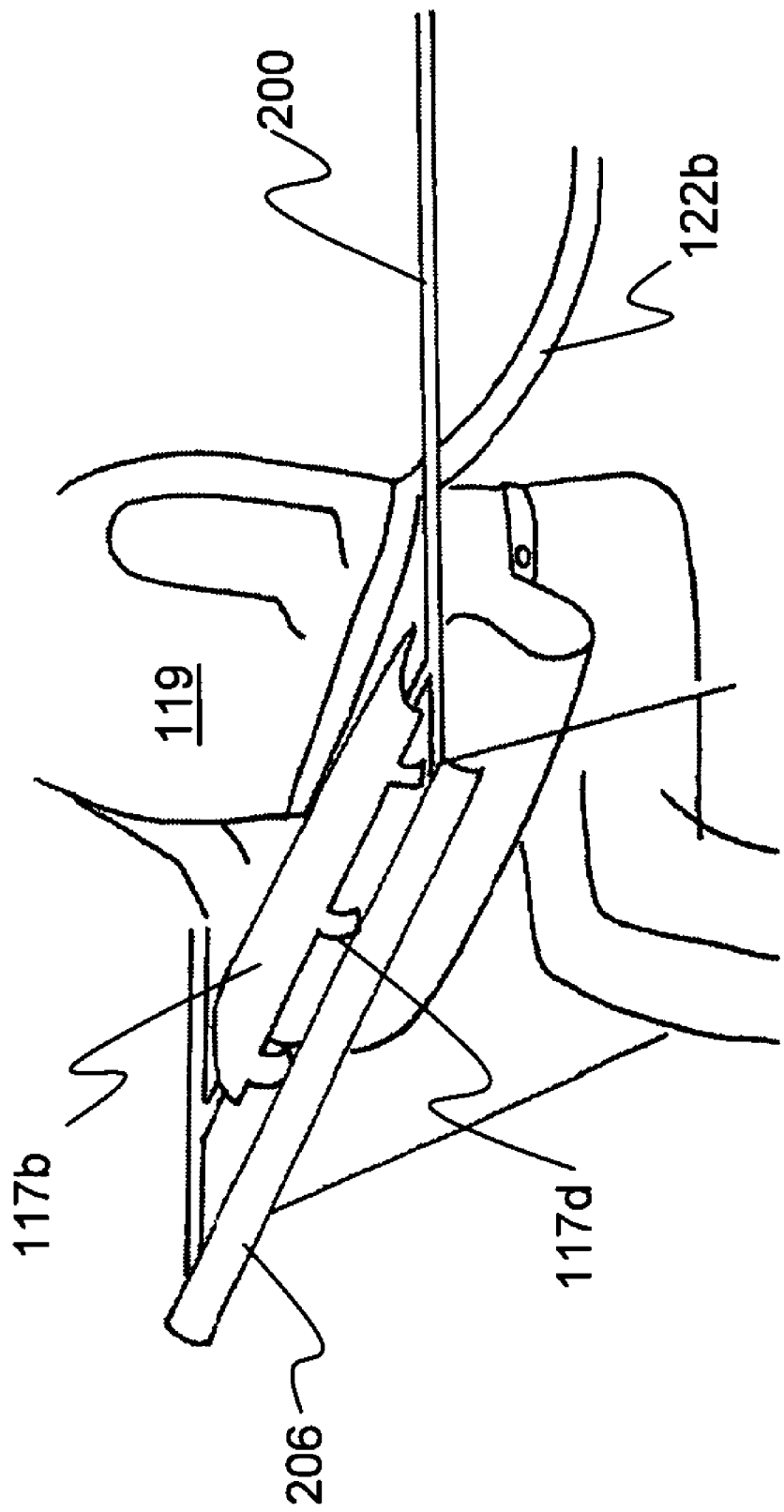
Figure 24:
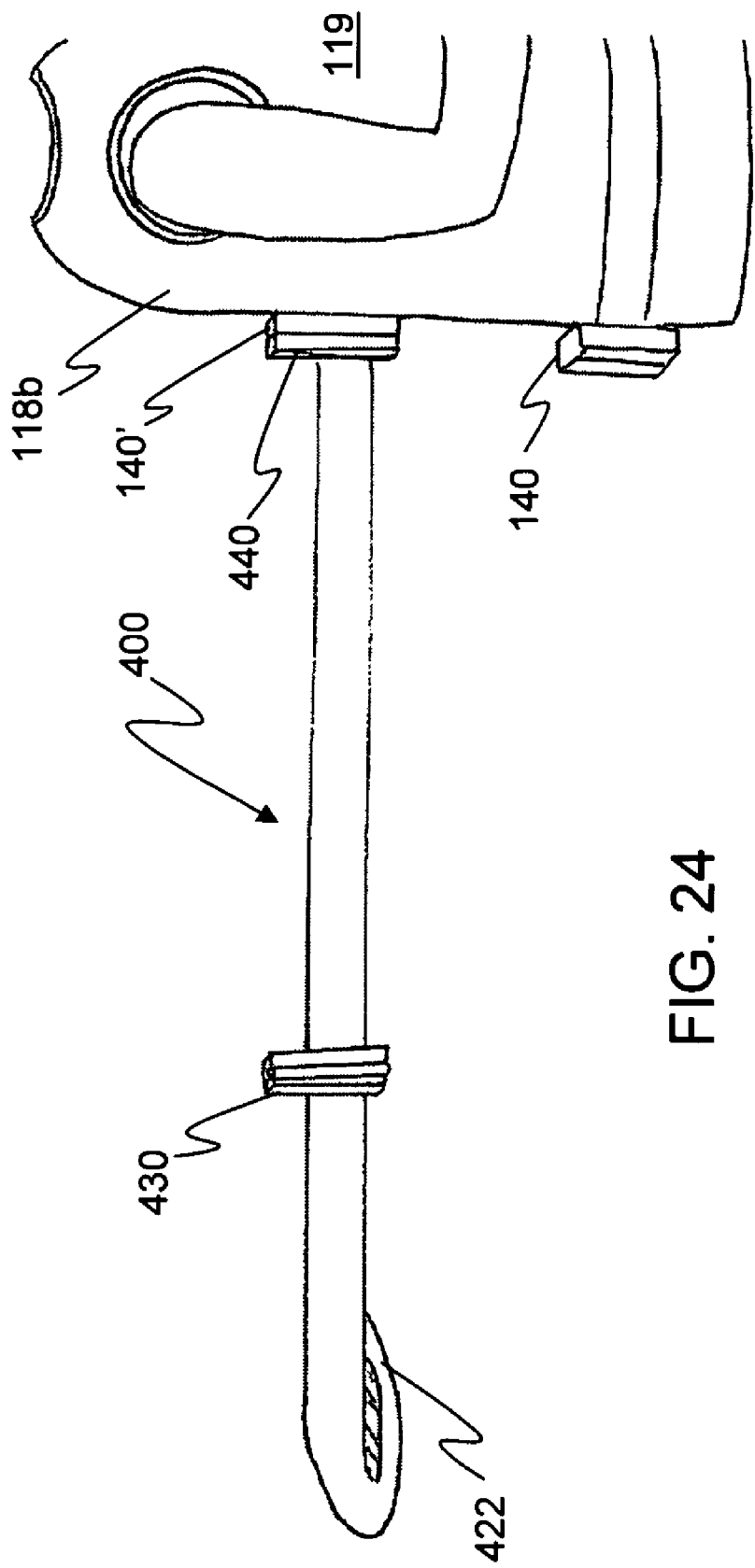
FIG. 24 shows the strap of FIG. 20 secured to the vest of FIG. 1.

As shown in FIGS. 23A-23C, in some embodiments, a durable (reusable) garment 100 may have a means for attaching a disposable or washable hygienic panel 117 in the front or back or both sides of the vest, for hygienic purposes. This can protect the child from contaminated surfaces of shopping carts and restaurant high chairs, by forming a barrier between the child and a dirty surface. This attaching means may be hook and loop fasteners, buttons, snaps, ties, adhesive tapes, zippers or the like. The hygienic panel may have a variety of shapes. FIG. 23B shows a hygienic lap portion 117a. FIG. 23B shows a relatively small panel 117a which widens to form an attachment panel 117b. The panel 117a rests on the child's thighs, and end 117b is placed directly on top of the grab bar of the cart 200 or highchair 300. The end 117b of lap panel 117a may have an attachment means at its bottom, such as hook and loop fasteners 117c, to attach the hygienic panel to the handle bar 206 of the shopping cart 200 (FIG. 23C) or the grap bar of a highchair 300. The bottom fasteners 117c allow the lap portion 117a to be attached to the handle bar 206 of a shopping cart 200 (FIG. 23C) or grab-bar of a stroller (not shown). The separate hygienic panel 117 allows use of a water repellant fabric for the outside of the durable portions 118a, 118b, 119 of vest 110, and a less expensive, more absorbent disposable material for the hygienic panel 117. It also allows the hygienic panel 117 to be removed temporarily, for example, if the garment is to be worn in a more formal setting. Although a particular exemplary shape of panel 117 is shown, the shape may be varied. For example, a trapezoidal lap portion may be provided, with a narrower end at the connecting portion.

In other embodiments, an integrally attached flap may serve as the hygienic panel 117. The flap 117 may be joined to the side 119 of garment 100 by stitching, adhesives, or the like. The flap 117 may be made of the same or different material as the outer layer of the vest 110. The flap may include a lap portion 117*a*.

FIG. 23A shows an optional narrow storage pouch 160 that may be included at the bottom of side 119' of the vest 110'. Other components of vest 110' may be the same as described above, and descriptions thereof are not repeated. The pouch may have fasteners, such as snaps 161, hook and loop, buttons, ties or the like. The hygienic panel 117 may be stowed inside the pouch 160 when not in use. The panel 117 may be unfurled from the pouch 160 for use, as shown in FIG. 23B. One end (not shown) of the hygienic panel 117 is secured (e.g., by snaps, hook and loop, or by sewing) to the inside of the pouch 160. In some embodiments, only the lap portion 117 of the hygienic panel is included.

In other embodiments, an optional bib portion (not shown) may be included, and may be sewn into pouch 160 above the lap portion 117. The bib portion would be unfurled upwardly and its top would connect (e.g., by snaps or hook and loop fasteners) to the front of the vest 110, whereas the lap portion 117 is unfurled downwardly. Either or both the bib portion and/or the lap portion 117 may be unfurled as appropriate in any given situation. The lap portion 117 and the bib portion (not shown) by be connected to each other by a connecting strip (not shown) that serves as the point of attachment to the inside of the pouch 160.

In some embodiments, contact information can be written on a panel 104 (FIG. 2) within the lining of the vest 110, e.g. caregiver's house/cell phone number, allergies and any pertinent medical information, which would be useful should a child become lost while wearing the vest 110.

By adding a panel 104 (shown in phantom in FIG. 2 to indicate hidden lines) to the inner lining of the vest 110, optionally with a transparent plastic cover panel, a location is provided where contact and pertinent health information can be written. Such information would be valuable, should a child become lost while wearing the vest 110. Information such as a caregiver's land and/or cell phone number, child's name, medical information and allergies could be written on the panel. The information would not be visible while the garment is being worn, protecting privacy, when written on the vest's inner lining.

Optionally, a pocket 106 (shown in FIG. 2) could be placed on Side 119 of the vest 110. The vest 110, being of a soft, flexible material could be folded on itself by turning the pocket inside out. A short strap or webbing, or cord or ribbon 108 with a snap fastener could be attached to the inner lining of the pocket. When the vest 110 is being worn, a pacifier 107 could be attached using the snap fastener, keeping it accessible and convenient for the child. The length of the a webbing/cord/ribbon 108 for attaching the pacifier 107 should be short enough as not to pose a strangulation threat. When the pocket 106 is turned inside out and the vest 110 is contained within, the webbing/ribbon/cord with snap fastener could be used to attach the system to a diaper bag etc. for future use, keeping the system accessible. Alternatively, the hygienic panel 117 may be stored in the pocket, when the hygienic panel 117 is not being used.

The vest 110 may be provided, in a disposable form. Rather than a durable material, a paper or disposable diaper material could be used to form the vest, lightweight webbing and the same male/female fastener components 130, 140 could be used. It could then be used on shopping carts 200 and as a disposable form of vest in domestic/restaurant highchairs 300 when connected to the reusable attachment strap 420. Retailers' logos 102 could be printed on Side 119 and used as an advertising tool. By printing the advertising information on a disposable portion of the garment, opportunities are created to solicit repeat advertisements from advertising clients, to restock the supply of disposable vests.

In some embodiments, either or both of the fastener system components 130, 140 may slide along the length of the attachment strap 120 to change its operative length.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:
1. A safety device, comprising:
a garment shaped to be worn on a torso of a user;
a flexible strap attachable to the garment and extending from the garment on first and second sides thereof, the strap having first and second ends;
an elongated first fastener component attached at or near the first end of the strap, the first fastener component having a longitudinal direction and being positionable in either a first orientation with the longitudinal direction of the first fastener component oblique or substantially normal to a portion of the strap at or near the first end thereof, or a second orientation with the longitudinal direction of the first fastener component aligned or nearly aligned with a portion of the strap at or near at the first end thereof; and
an elongated second fastener component attached at or near the second end of the strap, the second fastener component having a longitudinal direction and being positionable in either a first orientation with the longitudinal direction of the first fastener component oblique or substantially normal to a portion of the strap at or near the second end thereof, or a second orientation with the longitudinal direction of the second fastener component aligned or nearly aligned with a portion of the strap at or near at the second end thereof,
wherein the first and second fastener components are capable of locking engagement with each other while joined in the first orientation, and are shaped for being used individually as anchors while in the first orientation and separated from each other, and
wherein the first and second fastener components are longer than a width of the strap, the first and second fastener components have respective centroids, and the strap is attached to the respective first and second fastener components at respective locations that are offset from the respective centroids along the lengths of the first and second fastener components.
2. The device of claim 1, wherein
the first fastener component includes a male portion, and the second fastener component includes a female portion having an opening at least at one end thereof, for slidably receiving the male portion, and
at least one of the first and second fastener components includes means for retaining the other of the first and second fastener components upon engagement therewith.

3. The device of claim 2, wherein the male portion includes a portion shaped as an elongated cylinder, and the female portion includes an elongated cylindrical opening.

4. The device of claim 1, wherein the first fastener components has a length from about 5 cm (2 in.) to about 9 cm (3.5 in), a width of about 2 cm (¾ in) or less, and a height of about 2 cm (¾ in) or less, and the strap is attached to the respective first and second fastener components at respective locations that are longitudinally offset from the respective centroids of the first and second fastener components by a distance from 0.6 cm (¼ in) to 3.6 cm (1-½ in).

5. The device of claim 1, wherein at least one of the first and second fastener components has a recessed attachment member, to which the strap is attached.

6. The device of claim 1, wherein the garment is a vest.

7. The device of claim 1, wherein the garment includes at least one region capable of having advertising indicia placed thereon.

8. The device of claim 1, further comprising a storage pouch on one side of the garment, and an attached or attachable hygienic panel that is stowable in the storage pouch.

9. A method comprising:
placing a garment on a torso of a user;
providing a flexible strap attached to the garment, the strap having first and second ends extending from the garment on first and second sides thereof, the strap having an elongated first fastener component attached at or near the first end of the strap at an attachment location part way along a length of the first fastener component, the strap having an elongated second fastener component attached at or near the second end of the strap at an attachment location part way along a length of the second fastener component, wherein the first and second fastener components are capable of locking engagement with each other;
inserting each of the first and second fastener components through respective first and second openings in at least one wall or frame of a vehicle in which the user is located, wherein each of the first and second fastener components has a length that is greater than a dimension of the first and second openings, respectively, and
rotating the first and second fastener components to orientations substantially parallel to portions of the at least one wall or frame of the vehicle having the respective first and second openings, to anchor the first and second fastener components to the frame, wherein the rotating step includes anchoring the first and second fastener components to the frame by interference between the first and second fastener components and the first and second openings, respectively, without locking engagement.

10. The method of claim 9, wherein the first and second fastener components are longer than a width of the strap, the first and second fastener components have respective centroids, and the strap is attached to the respective first and second fastener components at respective locations that are offset from the respective centroids along the lengths of the first and second fastener components.

11. The method of claim 9, wherein the vehicle is a shopping cart, the first and second fastener components each have a width and height that are smaller than a smaller dimension of an opening of the frame of the shopping cart, and the first and second fastener components each have a length that is greater than the smaller dimension of the opening of the frame of the shopping cart.

12. The method of claim 9, wherein the vehicle is a shopping cart, and the wall is a fixed wall of the shopping cart.

13. The method of claim 12, wherein the garment is a vest.

14. The method of claim 13, further comprising placing the child in a seat of the shopping cart before the inserting step, wherein the inserting step includes inserting the first and second fastener components in first and second openings of the shopping cart located behind and below the child.

15. The method of claim 14, further comprising selecting the first and second openings so that the first and second openings are out of reach of the child.

16. The method of claim 9, further comprising:
transferring the user between the vehicle and a seat while the user wears the garment;
wrapping the strap around, under or through the seat; and
locking the first and second fastener components to each other, to secure the user to the seat.

17. The method of claim 9, further comprising:
transferring the user between the vehicle and a seat while the user wears the garment;
locking the first and second fastener components to respective complementary fastener components on a second strap, the first and second straps forming a loop that is wrapped under, around or through the seat to secure the user to the seat.

18. The method of claim 9, wherein each of the first and second fastener components has a length that is greater than at least one dimension of the openings.

19. The method of claim 9, further comprising:
providing advertising indicia on the garment.

20. A method comprising:
placing a garment on a torso of a user;
providing a flexible strap attached to the garment, the strap having first and second ends extending from the garment on first and second sides thereof, the first and second ends having respective first and second fastener components that are capable of locking engagement with each other;
securing the user to a first object by joining the first and second fastener components to each other to form a closed loop for attachment to the first object; and
anchoring the garment to walls or a frame of a second object by:
inserting the first and second fastener components through respective first and second apertures in the walls or frame of the second object, and
rotating the first and second ends to be substantially parallel to the walls or frame having the apertures, the first and second fastener components being longer than a dimension of the apertures, including anchoring the first and second fastener components to the frame by interference between first and second fastener components and the first and second apertures, respectively, without locking engagement.

21. The method of claim 20, wherein the first and second fastener components are longer than a width of the strap, the first and second fastener components have respective centroids, and the strap is attached to the respective first and second fastener components at respective locations that are offset from the respective centroids along the lengths of the first and second fastener components 22. The method of claim 20, wherein the first object is a seat, and the second object is a shopping cart.

23. A method comprising:
placing a garment on a torso of a user;
providing a first flexible strap attached to the garment, the first flexible strap having first and second ends extending from the garment on first and second sides thereof, the first and second ends having respective first and second fastener components that are capable of locking engagement with each other;

securing the user to a first object by joining the first and second fastener components of the first strap to complementary first and second fastener components of a second strap, to form a closed loop for attachment to the first object; and anchoring the garment to walls or a frame of a second object while the user is not secured to the first object, by:
  inserting the first and second fastener components through respective first and second apertures in the walls or frame of the second object, and
  rotating the first and second ends to be substantially parallel to the walls or frame having the apertures, the first and second fastener components being longer than a dimension of the apertures, including anchoring the first and second fastener components to the frame by interference between first and second fastener components and the first and second apertures, respectively, without locking engagement.

24. The method of claim 23, wherein the first and second fastener components are longer than a width of the first strap, the first and second fastener components have respective centroids, and the first strap is attached to the respective first and second fastener components at respective locations that are offset from the respective centroids along the lengths of the first and second fastener components

25. The method of claim 23, wherein the first object is a chair, and the second object is a shopping cart.

26. The method of claim 23, further comprising:
removing the user from the first object;
attaching the second strap to the garment, and
allowing the user to walk while the tether is attached.

* * * * *